(12) United States Patent
Parodi et al.

(10) Patent No.: US 9,597,172 B2
(45) Date of Patent: Mar. 21, 2017

(54) RETRIEVAL CATHETER

(75) Inventors: Juan C. Parodi, Pinecrest, FL (US);
John Cheer, Manasquan, NJ (US);
Edward H. Cully, Flagstaff, AZ (US);
Michael J. Vonesh, Flagstaff, AZ (US);
Jeremy P. Young, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 46 days.

(21) Appl. No.: 11/864,354

(22) Filed: Sep. 28, 2007

(65) Prior Publication Data
US 2009/0088790 A1 Apr. 2, 2009

(51) Int. Cl.
*A61M 29/00* (2006.01)
*A61F 2/01* (2006.01)
*A61M 25/01* (2006.01)
*A61B 17/22* (2006.01)
*A61F 2/95* (2013.01)

(52) U.S. Cl.
CPC .... *A61F 2/013* (2013.01); *A61B 2017/22039* (2013.01); *A61F 2002/011* (2013.01); *A61F 2002/9528* (2013.01); *A61F 2002/9534* (2013.01); *A61F 2230/0006* (2013.01); *A61M 2025/018* (2013.01); *A61M 2025/0183* (2013.01)

(58) Field of Classification Search
CPC ........ A61B 17/12022; A61B 17/12145; A61B 2017/1205; A61B 17/3417; A61M 25/09; A61M 29/09041; A61M 25/01; A61M 25/0172; A61M 2025/018; A61M 2025/0183

USPC ... 606/191, 194, 200; 604/166.01, 160, 236, 604/264

See application file for complete search history.

(56) References Cited

U.S. PATENT DOCUMENTS

| | | |
|---|---|---|
| 3,472,230 A | 10/1969 | Fogarty |
| 3,682,173 A | 8/1972 | Center |
| 4,610,671 A | 9/1986 | Luther |
| 5,047,018 A | 9/1991 | Gay et al. |
| 5,053,004 A | 10/1991 | Markel et al. |
| 5,160,342 A | 11/1992 | Reger et al. |
| 5,205,822 A | 4/1993 | Johnson et al. |
| 5,263,932 A | 11/1993 | Jang |
| 5,342,297 A | 8/1994 | Jang |
| 5,391,172 A * | 2/1995 | Williams et al. ............ 623/1.11 |
| 5,409,459 A | 4/1995 | Gambale |

(Continued)

FOREIGN PATENT DOCUMENTS

| | | |
|---|---|---|
| EP | 0274129 | 5/1992 |
| EP | 0293605 | 8/1993 |

(Continued)

*Primary Examiner* — Katherine Rodjom

(57) ABSTRACT

A retrieval catheter operable by a single clinician that will neither displace a deployed stent nor cause undue trauma to the vascular lumen or lesion. The retrieval catheter may be sized to accommodate both a guidewire and a balloon wire. The retrieval catheter is easy to navigate through tortuous passageways and will cross a previously deployed stent or stent-graft easily with minimal risk of snagging on the deployed stent or stent graft. The sheath and dilator are adapted to allow a guidewire or balloon wire to pass through the walls of both and to allow the sheath and dilator to move axially with respect to each other.

10 Claims, 16 Drawing Sheets

(56) References Cited

U.S. PATENT DOCUMENTS

| | | | |
|---|---|---|---|
| 5,415,639 A | 5/1995 | VandenEinde et al. | |
| 5,458,615 A | 10/1995 | Klemm et al. | |
| 5,690,644 A * | 11/1997 | Yurek et al. | 623/1.11 |
| 5,827,322 A * | 10/1998 | Williams | 623/1.18 |
| 5,993,460 A | 11/1999 | Beitelia et al. | |
| 6,059,813 A | 5/2000 | Vrba et al. | |
| 6,165,197 A | 12/2000 | Yock | |
| 6,171,327 B1 | 1/2001 | Daniel et al. | |
| 6,193,691 B1 | 2/2001 | Beardsley | |
| 6,251,084 B1 | 6/2001 | Coelho | |
| 6,569,181 B1 | 5/2003 | Burns | |
| 6,669,716 B1 * | 12/2003 | Gilson et al. | 623/1.11 |
| 6,726,659 B1 | 4/2004 | Stocking et al. | |
| 6,929,652 B1 | 8/2005 | Andrews et al. | |
| 6,949,121 B1 * | 9/2005 | Laguna | 623/1.35 |
| 6,989,024 B2 * | 1/2006 | Hebert et al. | 623/1.11 |
| 7,153,320 B2 | 12/2006 | Euteneuer et al. | |
| 2002/0058963 A1 | 5/2002 | Vale et al. | |
| 2002/0120287 A1 | 8/2002 | Huter | |
| 2002/0121472 A1 * | 9/2002 | Garner et al. | 210/348 |
| 2002/0133118 A1 * | 9/2002 | Gerdts | A61F 2/95 604/103.04 |
| 2002/0161389 A1 | 10/2002 | Boyle et al. | |
| 2003/0004537 A1 | 1/2003 | Boyle et al. | |
| 2003/0093106 A1 | 5/2003 | Brady et al. | |
| 2003/0097095 A1 * | 5/2003 | Brady et al. | 604/164.13 |
| 2003/0153942 A1 | 8/2003 | Wang et al. | |
| 2003/0233117 A1 | 12/2003 | Adams et al. | |
| 2004/0059243 A1 * | 3/2004 | Flores et al. | 600/549 |
| 2004/0116832 A1 | 6/2004 | Friedrich et al. | |
| 2004/0167567 A1 | 8/2004 | Cano et al. | |
| 2004/0230286 A1 * | 11/2004 | Moore | A61F 2/95 623/1.11 |
| 2005/0090857 A1 | 4/2005 | Kusleika et al. | |
| 2005/0113862 A1 | 5/2005 | Besselink et al. | |
| 2005/0131449 A1 * | 6/2005 | Salahieh et al. | 606/200 |
| 2005/0137620 A1 * | 6/2005 | Alkhatib | A61B 17/22031 606/194 |
| 2005/0228439 A1 | 10/2005 | Andrews et al. | |
| 2006/0025805 A1 | 2/2006 | DoBrava et al. | |
| 2006/0058865 A1 * | 3/2006 | Case | A61F 2/95 623/1.11 |
| 2006/0074446 A1 * | 4/2006 | Gilson et al. | 606/200 |
| 2006/0129181 A1 * | 6/2006 | Callol et al. | 606/200 |
| 2006/0142703 A1 * | 6/2006 | Carter et al. | 604/264 |
| 2006/0167491 A1 | 7/2006 | Wholey et al. | |
| 2006/0190024 A1 * | 8/2006 | Bei | A61F 2/013 606/200 |
| 2006/0282149 A1 * | 12/2006 | Kao | 623/1.11 |
| 2007/0005101 A1 | 1/2007 | Fahey et al. | |
| 2007/0060943 A1 | 3/2007 | Dorn et al. | |
| 2007/0066992 A1 * | 3/2007 | Hanson et al. | 606/200 |
| 2007/0083215 A1 | 4/2007 | Hamer et al. | |
| 2007/0088382 A1 | 4/2007 | Bei et al. | |
| 2008/0262506 A1 * | 10/2008 | Griffin et al. | 606/108 |

FOREIGN PATENT DOCUMENTS

| | | |
|---|---|---|
| EP | 0388112 | 12/1993 |
| EP | 0556564 | 8/1997 |
| EP | 0592720 | 7/1998 |
| EP | 1127556 | 8/2001 |
| EP | 1346703 | 9/2003 |
| JP | 2007-501655 | 2/2007 |
| WO | 94/03213 | 2/1994 |
| WO | 94/15549 | 7/1994 |
| WO | 95/23007 | 8/1995 |
| WO | 98/39053 | 9/1998 |
| WO | 01/08743 | 2/2001 |
| WO | 01/34063 | 5/2001 |
| WO | 01/52768 | 7/2001 |
| WO | 02/069845 | 9/2002 |
| WO | 03/002033 | 1/2003 |
| WO | 03/068106 | 8/2003 |
| WO | 2004/098674 | 11/2004 |
| WO | 2005/013853 | 2/2005 |
| WO | 2006/091498 | 8/2006 |

* cited by examiner

RETRIEVAL CATHETER

FIELD OF THE INVENTION

The present invention relates to catheters used for retrieving, positioning, or repositioning endoluminal devices located distal or adjacent to a stent or other previously implanted device.

BACKGROUND OF THE INVENTION

The field of endovascular surgery is rapidly becoming an alternative to more traditional surgeries such as carotid endarterectomy, coronary artery bypass grafting, aortic aneurysm repair, and vascular grafting. Percutaneous intervention is becoming the primary means for revascularization in many such procedures. Distal embolization of friable debris from within the diseased conduit remains a risk of endovascular surgery, potentially involving complications such as myocardial infarction and ischemia. Devices such as balloon catheters and embolic filters have been used to control and remove embolic debris dislodged from arterial walls during endovascular procedures, distal to an interventional procedure site. Percutaneous introduction of these devices typically involves access via the femoral artery lumen of the patient's groin vasculature. An introducer sheath may then be inserted in the wound, followed by a guide catheter that is advanced to the site to be treated. A guidewire is usually introduced into the lumen of the vasculature and advanced distally, via manipulation by the clinician, to cross the lesion or area of treatment. Then a catheter containing the device(s) may be employed to traverse the length of the guidewire to the desired deployment location. Once the distal protection device is deployed, the lesion or stenosis is available for treatment.

A common practice for treating the lesion or stenosis is to deploy a stent at the target location to increase the lumen size of the vessel and maintain or increase patency. When feeding a guidewire through the lumen of a stent, there is a possibility that the tip of the wire will become diverted and/or ensnared by the stent. This possibility increases with increasing vessel tortuosity. This problem has been addressed through the use of a soft, flexible, floppy tip at the distal end of the wire to improve steerability and reduce the possibility of engaging the stent or peripheral vasculature. However, a flat-tipped catheter advanced over a guidewire with an inside diameter larger than the outside diameter of the guidewire, presents a sharp edge to the vessel or stent at the point of tangential contact. The exposure of this edge increases with vessel tortuosity and with an increase in differences between the guidewire outside diameter and catheter inside diameter.

Embolic filters and balloons are often deployed by traversing the lesion being treated and deploying the device distally. If a balloon wire or embolic filter becomes caught in the patient's vasculature or is otherwise prevented from removal by a stent, such as the device becoming entrapped within the struts of a stent, then the clinician is typically required to perform higher risk procedures to retrieve them. These include subjecting the device to greater retrieval forces, and removal through invasive surgical techniques. The former increases the risk of the device becoming detached from its guidewire or catheter, whereas the latter exposes the patient to the increased risks of open surgical extraction. Successful retrieval of these devices in situations other than those originally anticipated, without intimal dissection, plaque, hemorrhage, or vessel occlusion, is an important advancement in the field of interventional endovascular surgery.

SUMMARY OF THE INVENTION

A retrieval catheter assembly is described that may be operated by a single clinician and upon delivery will neither permanently displace a previously deployed stent nor cause undue trauma to the vascular lumen or lesion. The retrieval catheter assembly will enable a tubular retrieval sheath to be advanced over a wire between the outside diameter of a deployed stent and the vessel wall, or over a guidewire through the lumen of a stent and retrieve various devices, e.g., filters, balloons, etc. distal to the stent. The retrieval catheter may also enable a tubular sheath to be directed through the sidewall of a stent.

The retrieval catheter assembly comprises a sheath having a balloon wire or guidewire exchange port through the sidewall of the sheath and a dilator, which is positioned in the sheath lumen. The sheath has a body with relatively stiff proximal and distal sections and with a flexible middle section, which aids in the operation of the device. The dilator is adapted to slide axially relative to the sheath between an extended position and a retracted position while a balloon wire or guidewire extends through the exchange port. When the dilator is withdrawn in a proximal direction into the sheath, it provides a space within the lumen of the distal end of the sheath to accommodate a filter or other device retrieved by the wire.

The dilator includes a tapered tip, which allows the device to be inserted between the stent and the vasculature for retrieval of devices distal to the stent. The tip may be a soft or hard pliable thermoplastic, metal such as stainless steel, or ceramic and will have a radius, which averts snagging on the stent and vasculature. The inner diameter of the tip is sized to control the clearance between the tip inner diameter and the guidewire outer diameter, which aids in operation of the device.

The catheter assembly preferably includes a hydrophilic and/or a lubricious coating applied to the dilator tip and also preferably applied to the sheath from tip to the exchange port.

DETAILED DESCRIPTION OF THE INVENTION

Figure 1A:
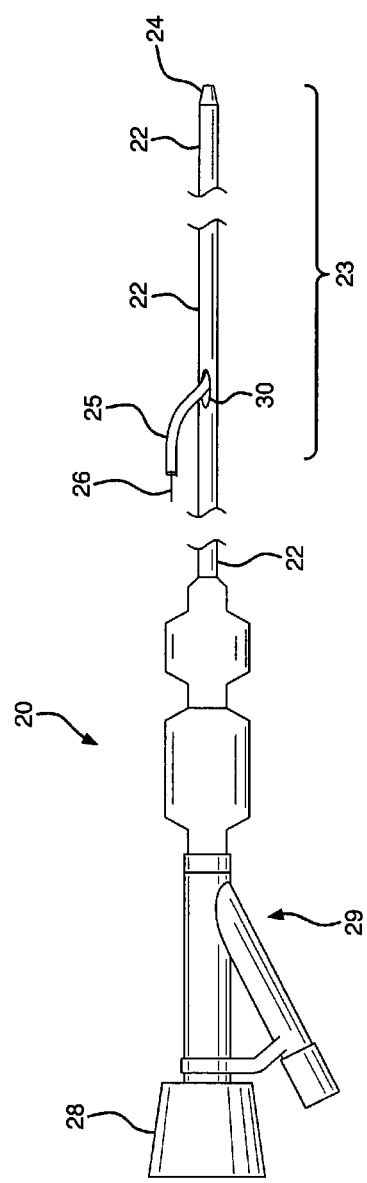
FIG. 1A is a perspective view of the catheter assembly.
Figure 1B:
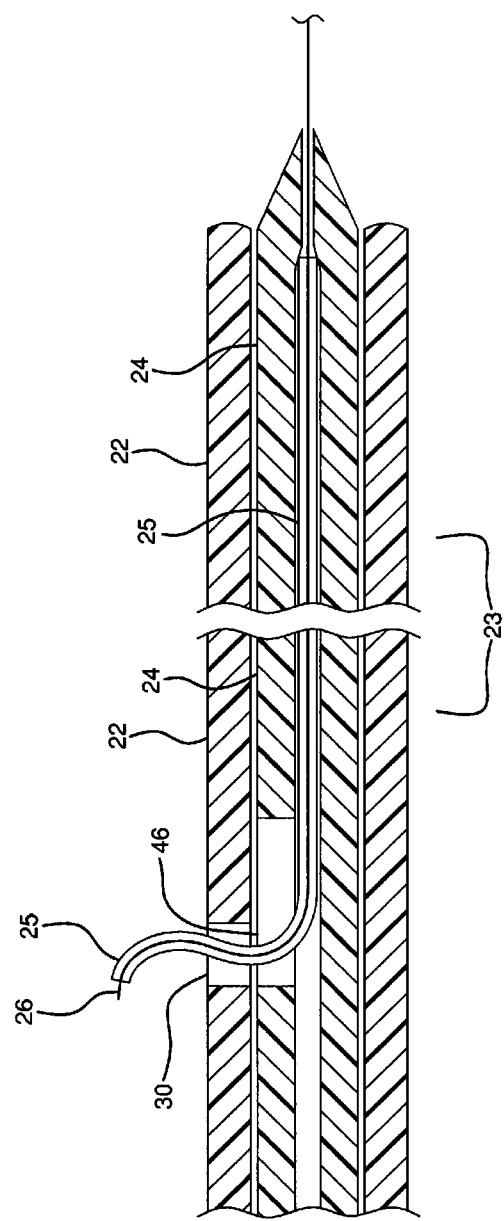
FIG. 1B is a longitudinal cross-sectional view of the catheter assembly tip with guidewire threading tube.

As noted above, this catheter assembly includes a sheath, dilator and guidewire. FIG. 1A is a perspective view of catheter assembly 20, having a sheath 22, dilator 24, guidewire threading tube 25, and guidewire 26. Guidewire threading tube 25 may be constructed from a variety of polymeric materials such as polyimide. Guidewire threading tube 25 is provided to aid in the insertion of the guidewire 26 through sheath slot 30 and dilator slot 46 (per FIG. 1B), prior to use in a patient. This threading tube 25 is typically removed from catheter assembly 20 prior to insertion into a patient. Also shown in FIG. 1A is the proximal end of the dilator 24, or dilator hub 28 extending from the luer hub 29.

Figure 1C:
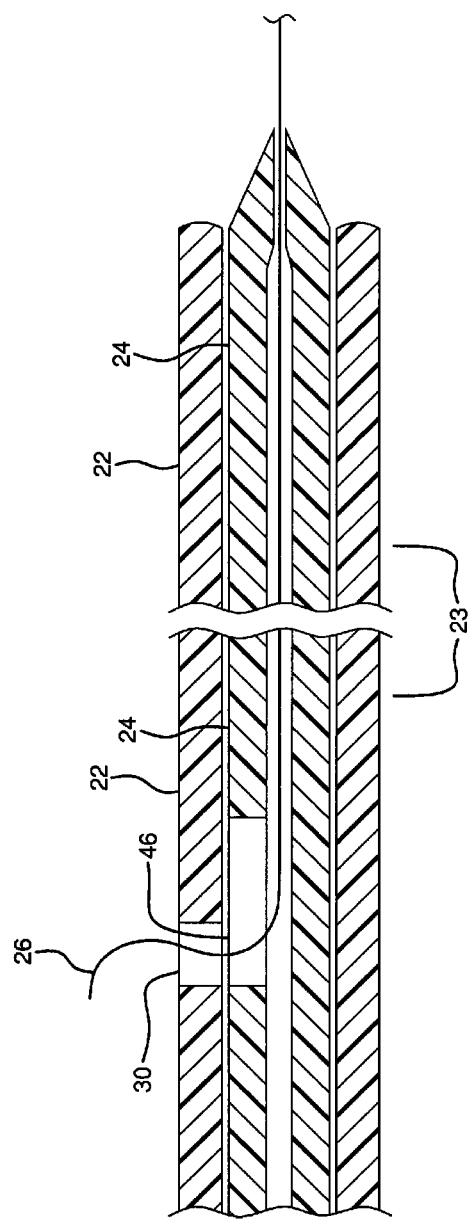
FIG. 1C is a longitudinal cross-sectional view of the catheter assembly tip and relative position of the cooperative opening region during a first stage of device retrieval.
Figure 1D:
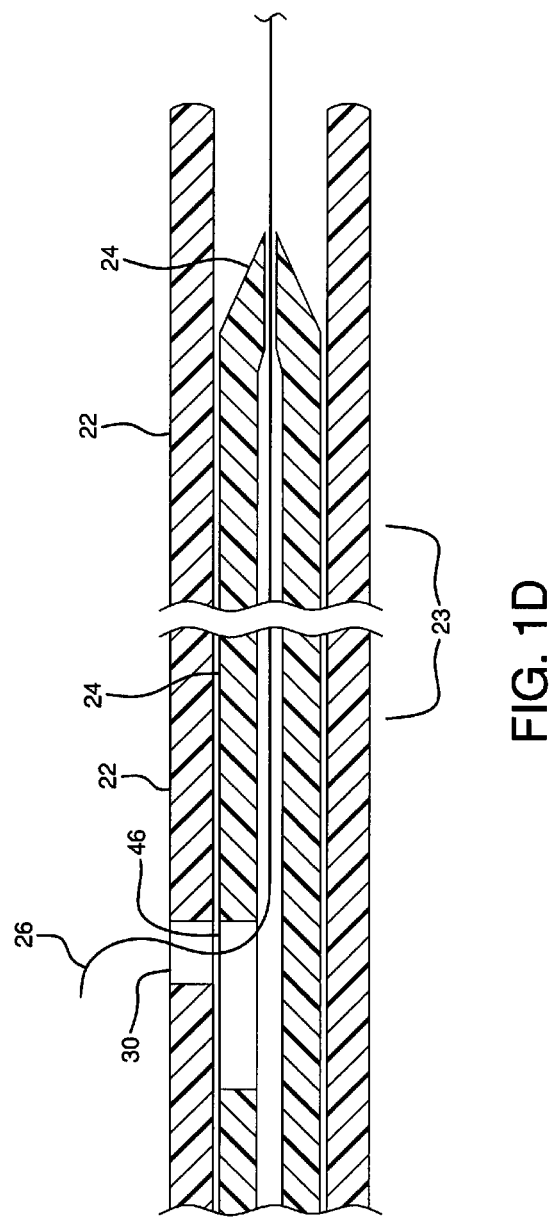
FIG. 1D is a longitudinal cross-sectional view of the catheter assembly tip and relative position of the cooperative opening region during a second stage of device retrieval.
Figure 1E:
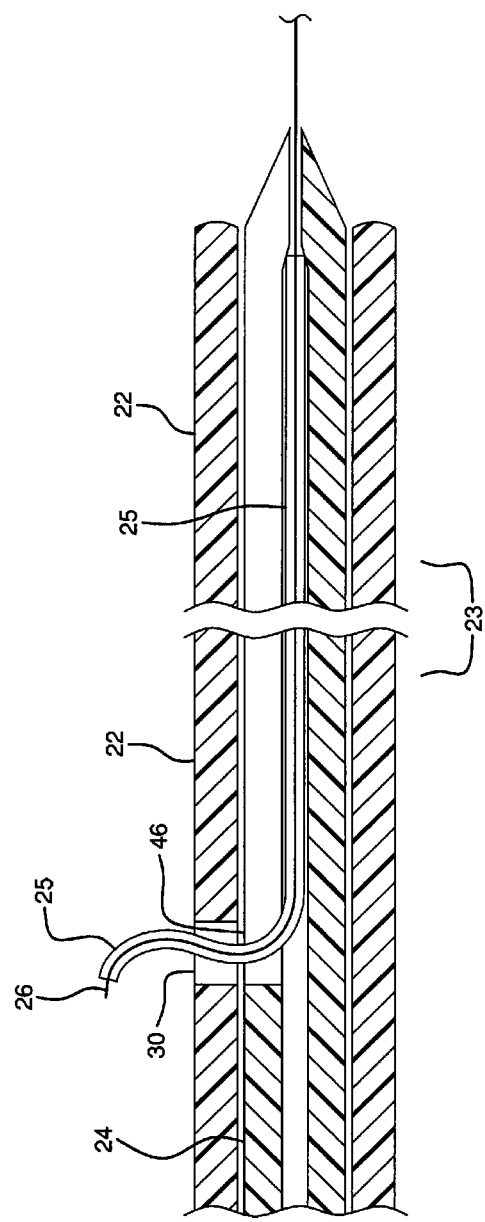
FIG. 1E is a longitudinal cross-sectional view of the catheter assembly tip configured to have a slit type cooperative opening extending to the most distal tip of the assembly.

FIG. 1A additionally depicts the distal section 23 of catheter assembly 20. FIGS. 1C-1E are longitudinal cross-sections of distal section 23 showing a sheath 22, dilator 24, dilator lumen 27, sheath slot 30, dilator slot 46, and guidewire 26. Note the relative distal movement of sheath 22 and sheath slot 30 with respect to dilator 24 and dilator slot 46. The sheath 22 and hubs 28 and 29 may comprise conventional medical grade materials such as nylon, acrylonitrile butadiene styrene, polyacrylamide, polycarbonate, polyethylene, polyformaldehyde, polymethylmethacrylate, polypropylene, polytetrafluoroethylene, polytrifluorochlorethylene, polyether block amide or thermoplastic copolyether, polyvinylchloride, polyurethane, elastomeric organosilicon polymers, and metals such as stainless steels and nitinol. The sheath 22 or dilator 24 may contain either radiopaque markers or contain radiopaque materials commonly known in the art.

Figure 2A:
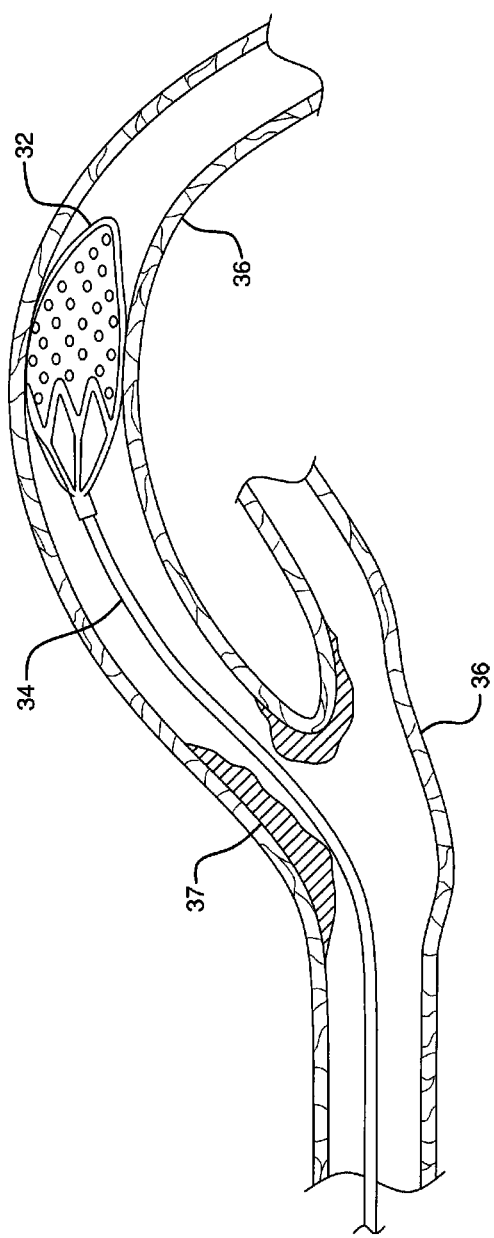
FIG. 2A is a cross-sectional view of a vascular filter in situ, distal to a vascular lesion.
Figure 2B:
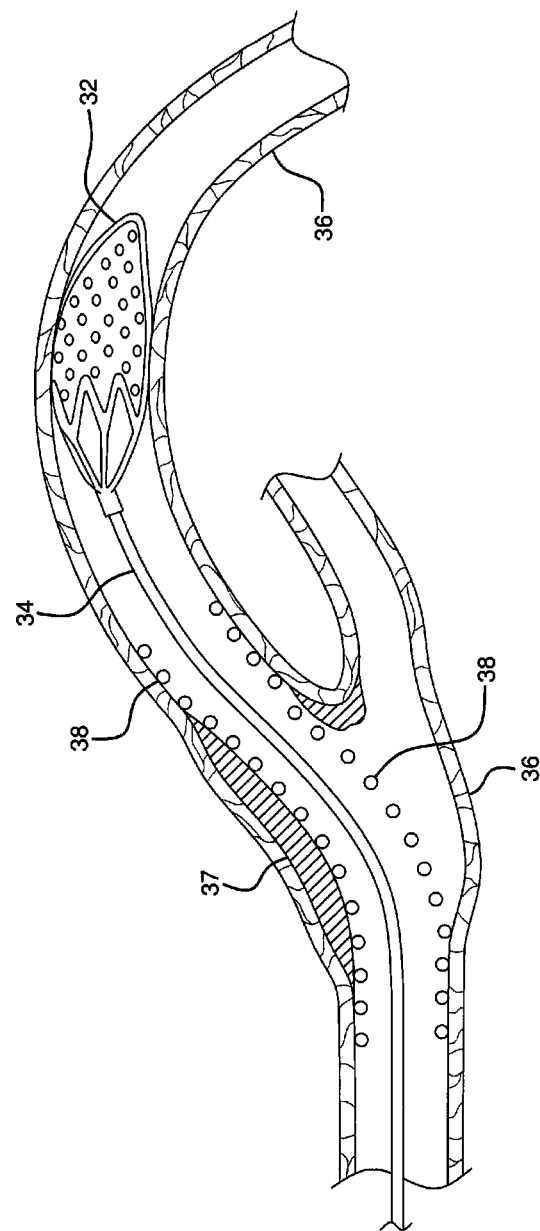
FIG. 2B is a cross-sectional view of a vascular filter in situ, distal to a vascular lesion that has been covered by a deployed stent.
Figure 2C:
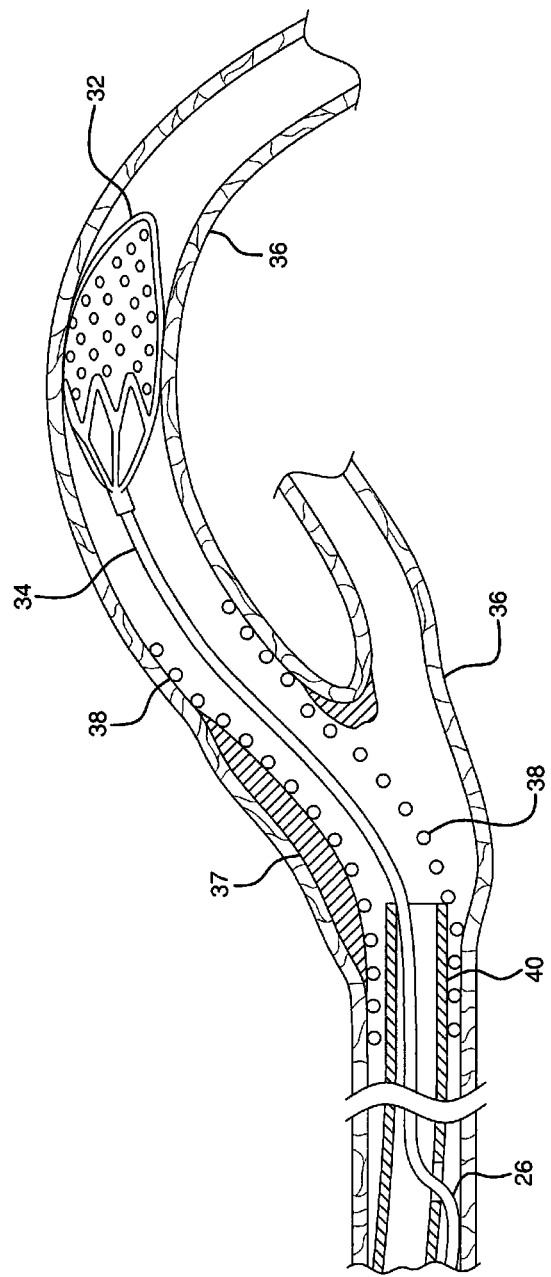
FIG. 2C is a cross-sectional view of a retrieval catheter of prior art.

In one embodiment, the catheter assembly 20 may be used to retrieve a previously placed vascular filter 32. FIG. 2A illustrates a vascular filter 32 with filter wire 34 placed within the vasculature 36, distal to a lesion 37. In this application, a stent 38 is placed over the vascular lesion 37 creating a rough, tortuous region across which vascular filter 32 is to be retracted as shown in FIG. 2B. FIG. 2C depicts a retrieval catheter 40 of prior art. Note the relatively inflexible catheter shaft and the inability of the catheter 40 to maintain a concentric position within the lumen of the catheter shaft of filter wire 34. Also note the significant difference between catheter 40 inner diameter and filter wire 34 outer diameter, creating an opening which provides an opportunity for catheter 40 to engage with the stent 38.

FIGS. 3A through 3D show sequential cross-sectional views of the retrieval catheter in use. In these figures, the catheter assembly 20 is used to retrieve a previously placed vascular filter 32.

Figure 3A:
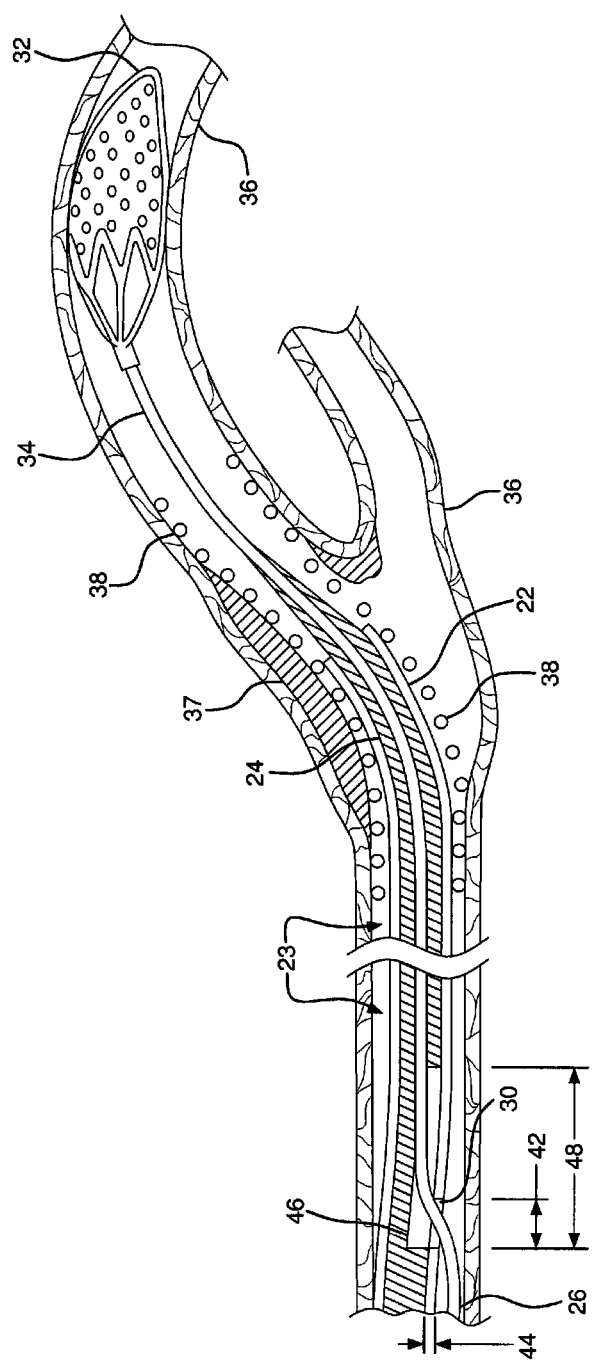
FIG. 3A is a cross-sectional view of one embodiment of this invention showing a step in a method of using the retrieval device in a vascular filter retrieval procedure.

FIG. 3A illustrates an embodiment of the present retrieval catheter with sheath 22 and dilator 24 navigating the rough, tortuous region through the stent 38 toward the previously placed vascular filter 32. The sheath 22 may be constructed with varying stiffness along the length. Methods of construction to achieve variable stiffness in a sheath component are well known in the art and include varying cross sectional profile dimensions and/or wall thickness, changing the hardness or modulus of the sheath material, braid modification, and including the use of a removable stylet or stiffening wire. Additional methods of achieving variable stiffness in a sheath component are generally taught by U.S. Pat. No. 6,858,024 and U.S. Pat. Appl. No. 2007/0088323 A1. The sheath 22 may be made with an outer diameter that would vary depending on targeted vascular size. For example, a sheath used with a 0.36 mm guidewire would have an outer diameter that ranges from about 1.57 mm to 1.62 mm. The sheath 22 inner diameter would also vary with application and for use with a 0.36 mm guidewire typically ranges from about 1.22 mm to 1.27 mm.

The sheath 22 includes a slot or aperture 30 functioning as a cooperative opening or exchange port through the sidewall of the sheath. The slot 30 may be formed through the side wall of the sheath 22 by methods known in the art which may include skiving by hand with a straight razor or cutting with a suitable tool. One or both ends of slot 30 may be formed to be perpendicular to the longitudinal axis of sheath 22. Alternately, one or both ends may be formed to have a taper to reduce the angle between the proximal end of slot 30 and the guidewire 26. As shown in FIG. 3A, the slot 30 may be a formed to have a length 42 that would vary with application but would preferably range from about 0.20 mm to 0.38 mm. Slot 30 may have a width 44 suitable to provide adequate clearance between the slot 30 and a guidewire 26 or balloon wire. Alternately, slot 30 may be formed as a slit thus providing an interference fit between the guidewire 26 or balloon wire and the slit walls. Slot 30 may also be configured with features to provide positive tactile feedback to a user during device use. These may include such features slot 30 being formed to have a barbell shape that provides stops at the proximal and distal ends of slot 30 for securing guidewire 26 or a balloon wire. Slot 30 may also be provided with rough surfaces or serrations along the edge of the slot 30 to provide enhanced tactile feedback. The slot 30 may be cut at a distance from the distal end of the sheath from about 1 cm to about 50 cm from the distal end of the sheath 22 depending on the specific design requirements. Preferably, the range would be from about 5 cm to about 31 cm from the distal end of the sheath 22. The most preferred range would be from about 25 cm to about 32 cm from the distal end of the sheath 22.

The outer surface of sheath 22 may be provided with a hydrophilic/lubricious coating. The coating may be applied to the entire outer surface of the sheath. Most preferably, the coating may be applied from the most distal end continuing to about the slot 30 or aperture. The inner surface of sheath 22 component may be provided with a hydrophilic/lubricious coating. The coating may be applied to the entire inner surface of the sheath 22. Preferably, the coating may be applied to the distal most 40 cm of the sheath 22. Most preferably, the coating may be applied to the distal most 30 cm of the sheath 22. The coating may be any biocompatible polymer lubricant as commonly known in the art.

Dilator 24 is typically formed from a lubricious plastic material such as polytetrafluoroethylene, polyethylene, polyether block amide or thermoplastic copolyether to provide a high degree of lubricity in the blood vessel as well as with respect to movement of the sheath 22 over the dilator 24. Dilator 24 may also be formed of a lubricious plastic material in combination with a metal hypo tube. Dilator 24 is typically provided with a hub 28 at its proximal end and is of a length slightly greater than the length of the catheter assembly so that when the hub 28 of the dilator is advanced fully distally against the proximal end of catheter hub 29, the tip of dilator 24 will project beyond the distal end of the catheter. Thus, the length of dilator 24 will depend on the length of the sheath 22. The tip of dilator 24 is considered to be the tapered portion located at the distal most tip of dilator 24. A length of about 1 cm for the tapered portion will be applicable to most applications but could range from about 1 mm to 5 cm.

Dilator 24 may be made with an outer diameter sized to pass through the lumen of the sheath 22 with which it is intended to be and may be supplied in various sizes dependent on the application and catheter sheath inner diameter. A typical range of outer diameters for the intended application of retrieving a vascular filter or balloon would be from about 1.14 mm to 1.19 mm. The clearance between a guidewire 26 or balloon wire and the lumen of dilator 24 is relatively small and would vary dependent on intended use. For the intended application involving use over a guidewire, a typical inner tip diameter would be from about 0.38 mm to 0.43 mm. Alternately, dilator 24 may be used with a balloon wire where a typical inner tip diameter would be from about 0.48 mm to 0.53 mm. Dilator 24 has a lumen 27 adapted for passage of a guidewire or balloon wire. Diameters of dilator lumens 27 will vary with intended use. A typical dilator lumen 27, suitable for use with a guidewire 26, would be from about 0.48 mm to 0.53 mm. Alternately, dilator 24 may be made with a lumen 27 suitable for balloon wires, typically ranging from about 0.61 mm to 0.66 mm.

Dilator 24 may have a tip made of pliable thermoplastic such as Pebax® (polyether block amide or thermoplastic copolyether from Arkema, Beaumont Tex. 77704) or metal such as stainless steel, nitinol or any other material with appropriate stiffness, hardness and other properties suitable for use in the human body. The dilator tip may alternately be constructed of a combination of a biocompatible metal and thermoplastic in a variety of ways. The tip may also be of composite metal or ceramic and/or polymer construction.

As shown in FIG. 3A (and similar to the slot 30 through the sidewall of sheath 22), dilator 24 has a slot 46 through the sidewall of the dilator 24. The dilator slot 46 may be formed through the sidewall of the dilator 24 by methods well known in the art which may include skiving by hand with a straight razor cutting with a suitable tool. One or both ends of dilator slot 46 may be formed to be perpendicular to the longitudinal axis of dilator 24. Alternately, one or both ends may be formed to have a taper to reduce the angle between the proximal end of dilator slot 46 and the guidewire 26.

The dilator slot 46 may have a length 48 extending from about 1 cm proximal to the dilator tip to the distal end of the luer hub 29. Preferably, the dilator slot 46 may extend from about 1 cm proximal to the dilator tip to about 100 cm proximal to the tip. Most preferably, the dilator slot 46 may extend from about 1 cm proximal to the dilator tip to about 33 cm proximal to the tip. In still another embodiment, dilator slot 46 (particularly if configured as a slit as described below) may extend from the tip to about, for example, 33 cm proximal to the tip.

Dilator slot 46 may have a width 48 suitable to provide adequate clearance between the dilator slot 46 and a guidewire 26 or balloon wire. Alternately, dilator slot 46 may be formed as a slit thus providing an interference fit between the guidewire 26 or balloon wire and the slit walls. Dilator slot 46 may also be configured with features to provide positive tactile feedback to a user during device use. These may include such features dilator slot 46 being formed to have a barbell shape that provides stops at the proximal and distal ends of dilator slot 46 for securing guidewire 26 or a balloon wire. Dilator slot 46 may also be provided with rough surfaces or serrations along the edge the of dilator slot 46 to provide enhanced tactile feedback.

Figure 3B:
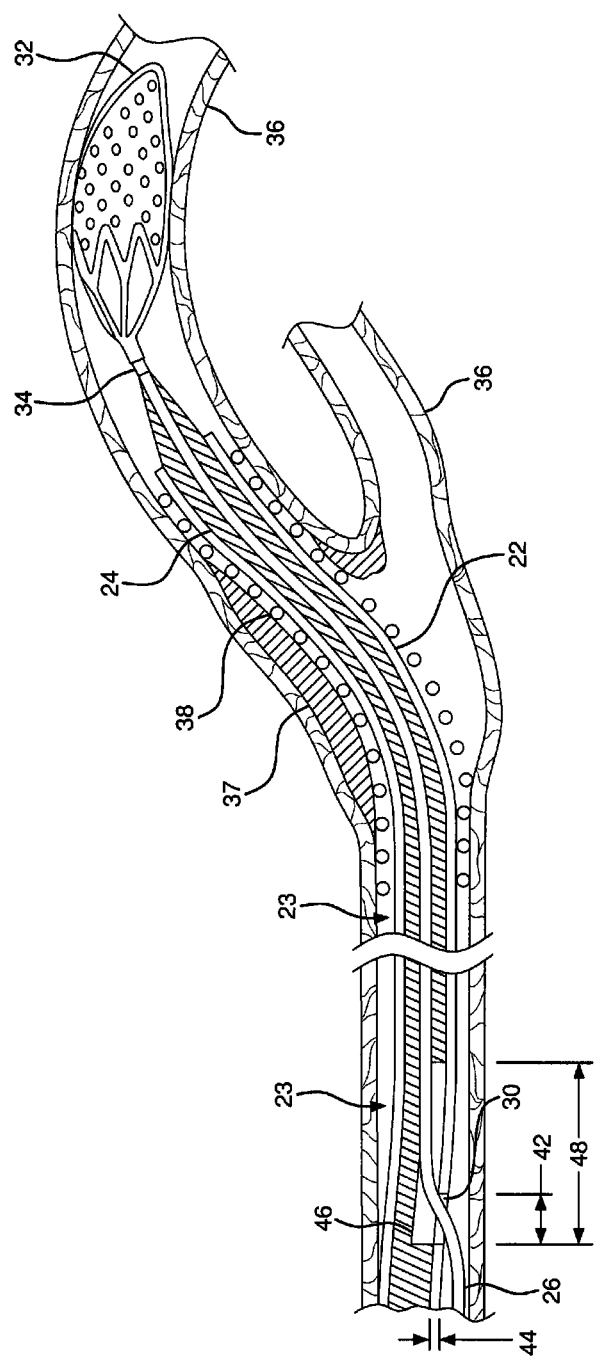
FIG. 3B is a cross-sectional view of one embodiment of this invention showing a second step in a method of using the retrieval device in a vascular filter retrieval procedure.

FIG. 3B shows the distal end of the catheter assembly 20 positioned in vasculature 36 in close proximity to a previously placed vascular filter 32. The catheter assembly 20 was advanced over the previously placed vascular filter wire 34. Note that dilator 24 protrudes from the sheath 22.

Figure 3C:
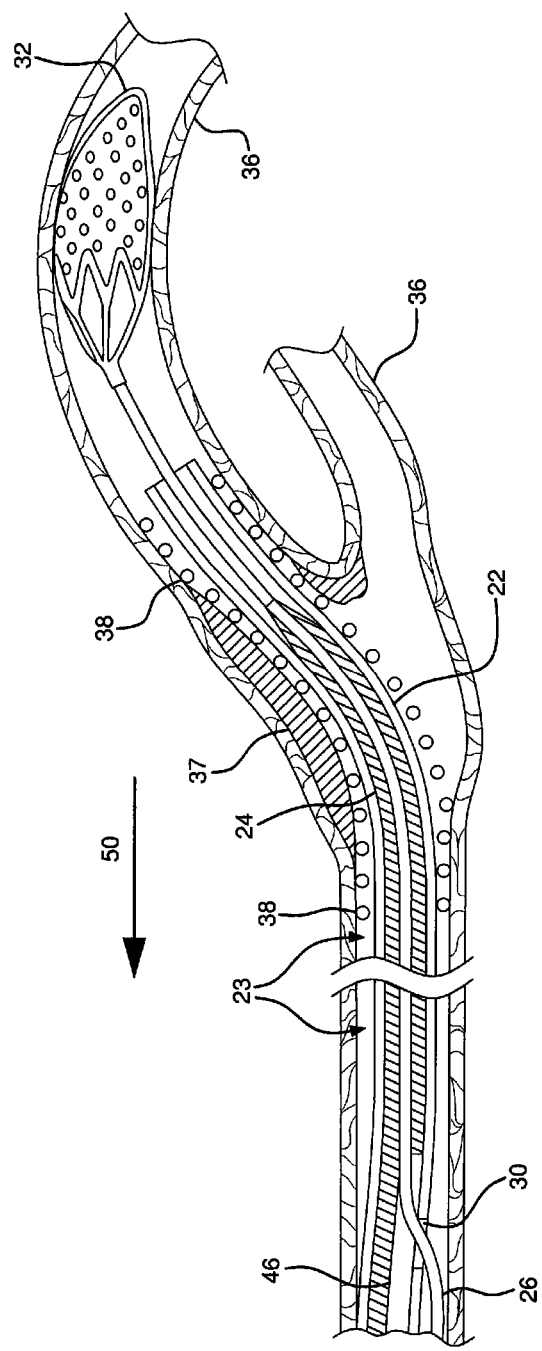
FIG. 3C is a cross-sectional view of one embodiment of this invention showing a third step in a method of using the retrieval device in a vascular filter retrieval procedure.

As shown in FIG. 3C, the dilator 24 is retracted into sheath 22 in the direction as shown by arrow 50. Note the axial sliding movement of slot 30 and dilator slot 46 with respect to slot 30 of sheath 22.

Figure 3D:
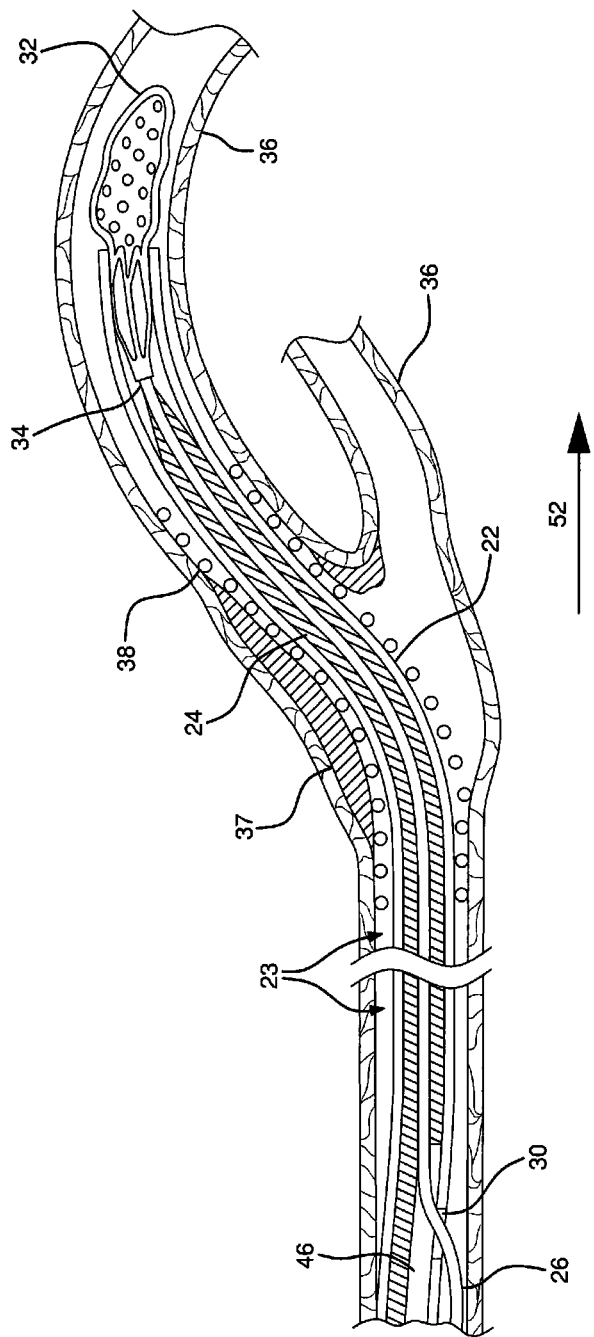
FIG. 3D is a cross-sectional view of one embodiment of this invention showing a fourth step in a method of using the retrieval device in a vascular filter retrieval procedure.

As shown in FIG. 3D, the dilator 24 remains retracted into the sheath 22. Sheath 22 is advanced in the direction as shown by arrow 52 thereby collapsing the vascular filter 32. After the filter 32 has been collapsed and contained within the sheath 22, the catheter assembly 20 is withdrawn from the target site.

Figure 4A:
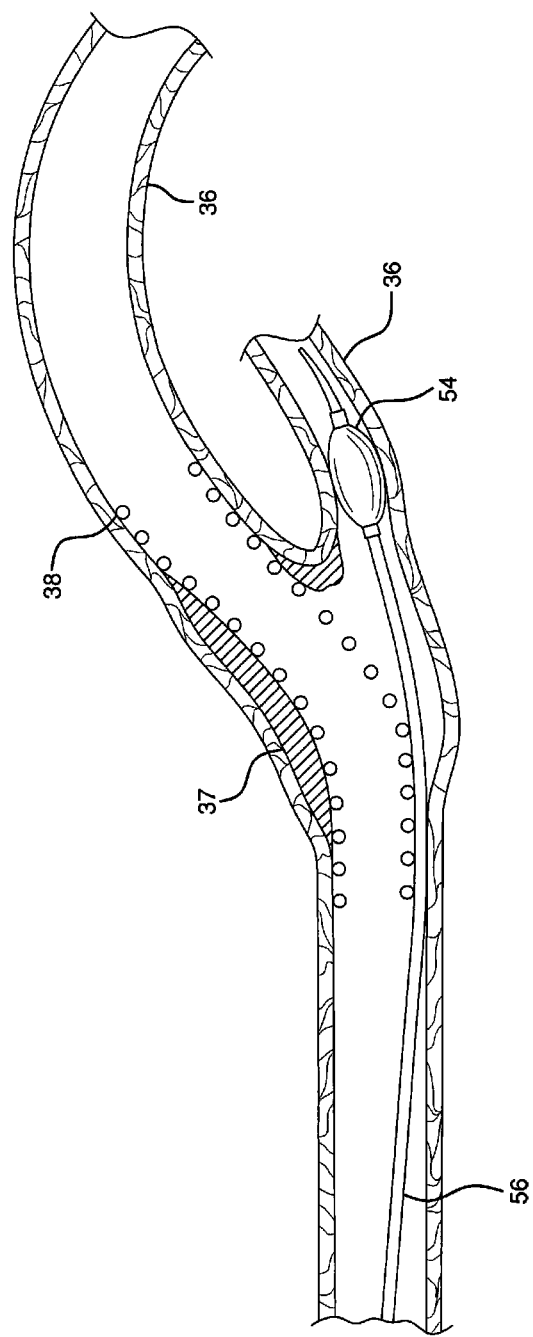
FIG. 4A is a cross-sectional view of an occlusion balloon with the balloon wire positioned between the deployed stent and the vasculature.
Figure 4B:
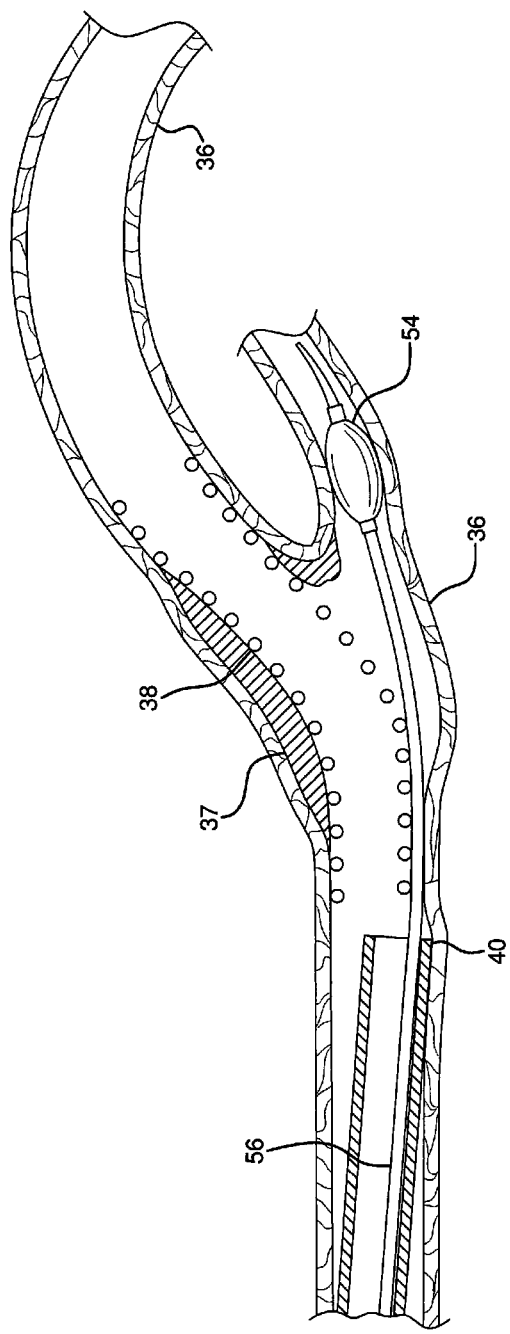
FIG. 4B is a cross-sectional view of a retrieval catheter of prior art.
Figure 4C:
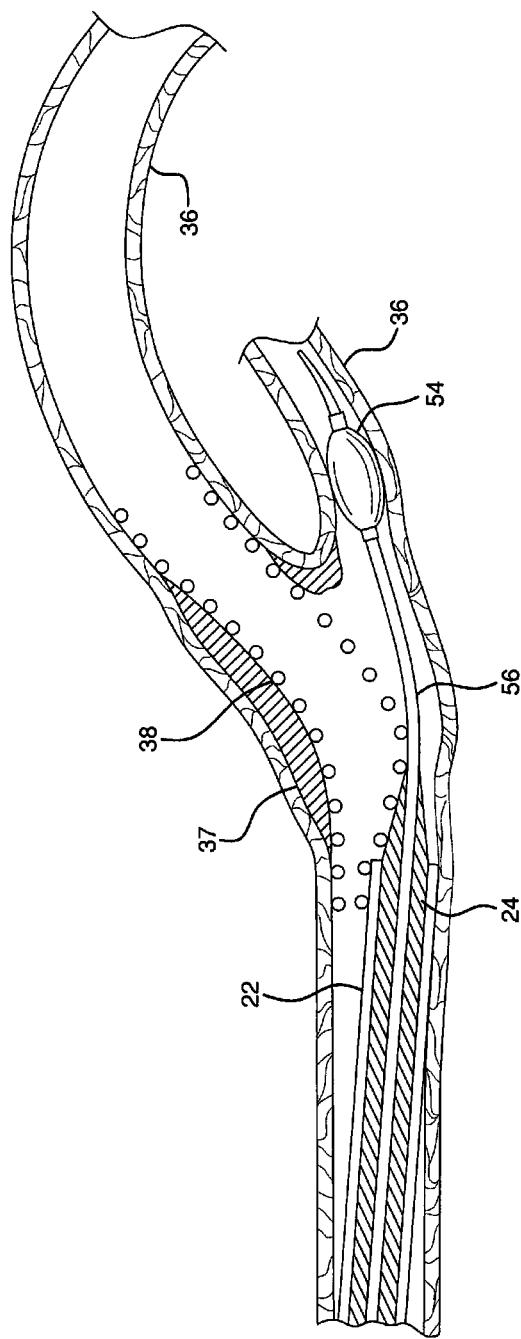
FIG. 4C is a cross-sectional view of one embodiment of the present retrieval catheter showing a step in a method of using the retrieval device in a balloon retrieval procedure.

FIGS. 4A through 4C show sequential cross-sectional views of a retrieval catheter in use retrieving a balloon 54.

FIG. 4A shows a stent 38 deployed over a balloon 54 and balloon wire 56, trapping the balloon 54 and/or balloon wire 56 between the stent 38 and vasculature 36.

FIG. 4B depicts a retrieval catheter 40 of prior art. Note the relatively inflexible catheter shaft and the inability of the catheter 40 to maintain a concentric position within the lumen of the catheter shaft of balloon wire 56.

FIG. 4C illustrates an embodiment of the invention with sheath 22 and dilator 24 navigating the rough tortuous region between the stent 38 and the vasculature 36 toward the trapped balloon 54. The remainder of the balloon retrieval procedure is similar to the procedure described in FIGS. 3B through 3D.

Figure 5:
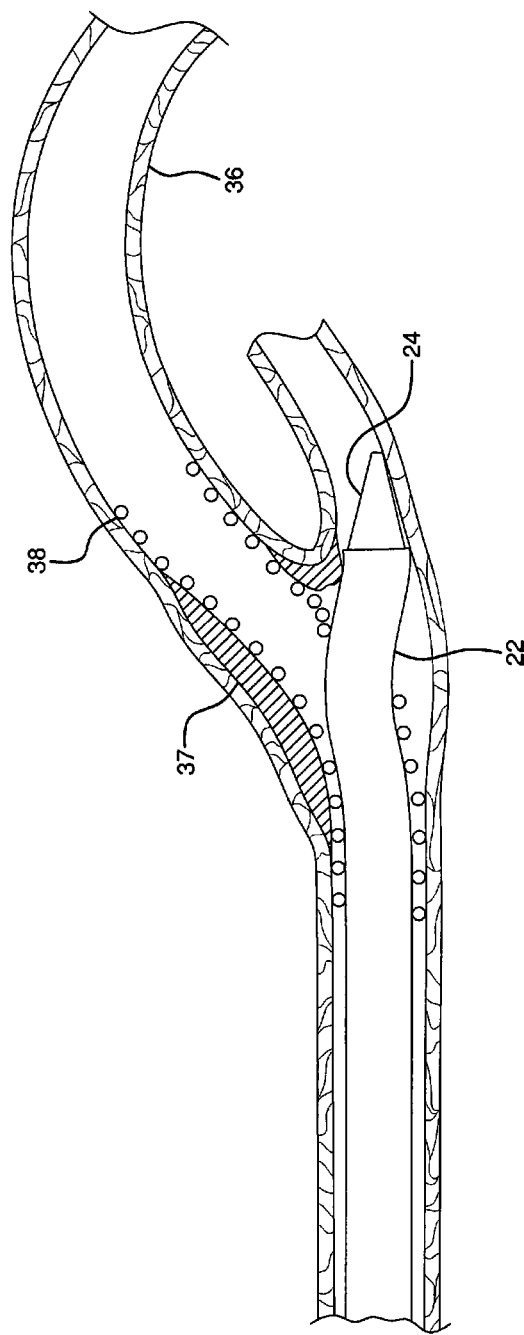
FIG. 5 is perspective view of one embodiment of the present retrieval catheter showing the retrieval catheter exiting the lumen of a previously placed stent through the sidewall of the stent.

The present invention may also be used to position or reposition a device located distal or adjacent to a stent or other previously implanted device. FIG. 5 depicts an embodiment of the present invention with sheath 22 and dilator 24 exiting the lumen of a previously placed stent 38 through the sidewall of the stent 38. This embodiment could be used to deploy or reposition an endoluminal device into the branch vasculature. The same embodiment could alternately be used to retrieve an endoluminal device from branch vasculature.

EXAMPLES

To construct a sheath, a 1.24 mm PTFE coated mandrel was loaded with a 1.29 mm inner diameter etched PTFE liner (1.29 mm inner diameter.×0.02 mm thick wall) and secured. A braided sleeving (0.25 mm×0.76 mm stainless steel flat wire, 2 over 2 under, 50 ppi) was loaded and secured at the proximal end of mandrel. The braid was stretched to the distal end of the mandrel and carefully trimmed to length with scissors so that the ends of the wires were uniform. Trimming of the braid length may be achieved with any suitable cutting or trimming tool. A marker band (platinum/iridium, 1 mm width minimum, inner diameter 14.7 mm, 0.25 mm minimum thickness) was slid onto the assembly from the proximal end of the loaded mandrel to the distal end. The marker band was carefully brought up to the end of the braid so that the marker band covered the end of the braid and so that no ends of wires were showing at the marker band. The location of the marker band should be from about 5.08 cm to 6.35 cm from the distal end of the mandrel. A hand crimper tool was used to secure the marker band. The braid was then stretched from the proximal end of the mandrel and re-secured.

To pre-assemble the proximal and distal body stock components of the sheath, the proximal component (Pebax® 7233, 72 durometer and 1.57 mm inner diameter and 0.10 mm wall, gold pigment) was cut to about 125 cm and the distal body stock component (Pebax® 5533, 55 durometer and 0.157 cm inner diameter and 0.10 mm wall, grey pigment) was cut to about 32.5 cm. The distal body stock component was flared with the end of a pair of small tweezers so that it would slide over the proximal body stock component. The distal and proximal components were loaded onto a 0.15 mm PTFE mandrel (nonporous PTFE) and the two components were overlapped by 1 mm. A 2.54 cm long length of FEP heat shrink (EP4587-10T, Zeus, Orangeburg, S.C. 29116) was positioned over the center of the 1 mm overlap of the two body stock components and a heat gun was used to bond the two components together. The FEP heat shrink tube was removed after the bond had cooled.

The pre-assembled body stock component was loaded onto the proximal end of the 1.24 mm PTFE coated mandrel bringing the end of the pre-assembled body stock component to within 2 cm to 3 cm past the marker band. A heat shrink tube (EP4587-10T FEP 1.9 mm minimum expanded inner diameter) was loaded over the entire assembly with the end of the heat shrink tube reaching the end of the pre-assembled body stock component distal end. The two ends were bonded together with a heat gun. The assembly was heated in a convection heat shrink reflow oven. The assembly was allowed to air cool, the heat shrink tube was removed and the ends were trimmed with a razor. The entire assembly was removed from the mandrel. The assembly was cut to a length of about 142 cm and the tip was trimmed. A hole was hand cut at about 29.7 cm from the distal end of the sheath. A female luer hub (Qosina part No. 41426 Qosina, Edgewood, N.Y. 11717) was bonded to the proximal end with adhesive (Loctite® 4011 Adhesive, Henkel Corp., Rocky Hill, Conn. 06067).

A stock dilator (Pebax® 7233, light grey pigment, 0.48 mm inner diameter×1.2 mm outer diameter) was tipped down to 0.36 mm inner diameter and 0.66 mm outer diameter with a radio frequency tipping machine (Ameritherm Inc., Scottsville, NY 14546). The dilator was then cut to about 152 cm in length. Any appropriate cutting method may be used. An 4.0 cm slot was hand skived in the dilator starting at about 27.2 cm from the distal end of the dilator. The proximal end of the dilator was heat flared to form a mechanical anchor. A female luer hub (Qosina part. No. 64018) was bonded onto the dilator proximal end with Loctite® 3311 Adhesive.

To assemble the catheter assembly 20, a hemostasis valve (part No. RV0317-000, Qosina part No. 88416) was attached to the hub of the dilator 24. With the aid of a 0.36 mm guidewire, the sheath 22 and dilator 24 components were assembled and guidewire threading tube 25 (Phelps Dodge part No. Polyimide EP4649-10Z 0.38 mm inner diameter× 0.47 mm outer diameter, Phelps Dodge HPC, Trenton, Ga. 30752) was installed in the assembly. The catheter assembly 20 was masked to expose the proximal and distal ends. A flexible mandrel (0.46 mm outer diameter) was inserted into the distal end of the assembly until it exited the cooperative opening 30. The loaded assembly was then placed into a vacuum plasma system. The entire assembly was plasma treated to enhance attachment of the polymer lubricant. The catheter assembly 20 was removed from plasma system. The sheath 22 and dilator 24 components of the catheter assembly 20 were then dip coated with a biocompatible polymer lubricant to reduce friction. The catheter assembly 20 with lubricious coating was then heat cured. The flexible mandrel was removed and catheter assembly 20 was then placed in a protective polymer coil and packaged for shipment.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. A catheter assembly, comprising:
   a tubular sheath having a lumen extending for its entire length, said tubular sheath further having a distal end, a sheath sidewall, outside and inside diameters and a sheath exchange port in the form of an aperture through the sheath sidewall; and
   a tubular dilator having a lumen extending for its entire length, said tubular dilator further having a dilator sidewall, outside and inside diameters, a tapered distal end having a fixed maximum outside diameter that does not exceed the inside diameter of the tubular sheath and is the same diameter as outside diameter of the tubular dilator, and a dilator exchange port in the form of a slot through the dilator sidewall wherein said slot has a length that is greater than a length of the aperture measured in a direction parallel to longitudinal axes of the sheath and dilator, said slot extending from a first end to the tapered distal end of the dilator, said dilator positioned in the sheath adapted to slide relative to the sheath between an extended position wherein the tapered distal end of the dilator extends beyond the distal end of the sheath and a retracted position wherein the tapered distal end of the dilator is fully withdrawn into the sheath;
   wherein the dilator and dilator exchange port are configured to slide between the extended and retracted positions while a guidewire extends through the sheath exchange port and dilator exchange port,
   an expandable medical device, the tubular sheath being configured to receive the expandable medical device distal to the dilator when the dilator is in the retracted position.

2. A catheter assembly as claimed in claim 1 wherein at least a portion of said guidewire extends through a guidewire threading tube wherein the guidewire threading tube extends through aperture of the tubular sheath and the slot and at least a portion of the lumen of the of the tubular dilator.

3. A catheter assembly as claimed in claim 1 configured for filter retrieval wherein the expandable medical device is a filter that may be drawn into the distal end of the sheath when the dilator is in the retracted position.

4. A catheter assembly as claimed in claim 1 configured for balloon retrieval wherein the expandable medical device is a balloon that may be drawn into the distal end of the sheath when the dilator is in the retracted position.

5. A catheter assembly according to claim 1 wherein the tubular dilator component comprises a lubricious plastic material.

6. A catheter assembly comprising:

a tubular dilator component having a length extending between a tapered distal end and a proximal end thereof and having a lumen extending for the entire length, said tubular dilator further having outside and inside diameters and a wall, said tubular dilator component having a slot extending through the wall thereof, said slot having a length extending along a portion of the length of the tubular dilator component, said slot being located nearer to the tapered distal end than to the proximal end of the tubular dilator component;

a tubular sheath component having a lumen extending for its entire length, said tubular sheath component located around the tubular dilator component, said tubular sheath component having outside and inside diameters and a wall and having a length extending between distal and proximal ends thereof, wherein the length of the tubular sheath component is less than the length of the tubular dilator component, said tubular sheath component having an aperture through the wall thereof, the aperture having a length that is shorter than the length of the slot through the wall of the tubular dilator and located so as to cooperatively align with the slot of the tubular dilator component to allow a guidewire to extend through the aperture and slot, the slot extending from a first end to the tapered distal end of the dilator, wherein the tapered distal end of the tubular dilator has a fixed maximum outside diameter that does not exceed the inside diameter of the tubular sheath and is the same diameter as outside diameter of the tubular dilator; and an expandable medical device captured within the tubular sheath distal to the tapered distal end of the tubular dilator.

7. A catheter assembly according to claim 6 further comprising a guidewire having a length wherein a portion of said length is contained within a guidewire threading tube, said guidewire extending through the tapered distal end of the tubular dilator component, and said guidewire within the guidewire threading tube extending through the slot of the dilator component and through the aperture of the tubular catheter component.

8. A catheter assembly according to claim 6 wherein the tubular dilator component and the tubular sheath components may be moved axially with respect to each other for a length at least equal to the length of the slot of the dilator component and wherein when moved along the length of the slot, the tubular dilator component and the tubular sheath component move from a first axial positional relationship wherein the tapered distal end of the tubular dilator component extends beyond the distal end of the tubular sheath component, to a second axial positional relationship wherein the distal end of the tubular sheath component extends beyond the tapered distal end of the tubular dilator component.

9. A catheter assembly according to claim 6 wherein the tubular dilator component and the tubular sheath component may be moved axially with respect to each other after a guidewire is inserted through both the aperture and slot.

10. A catheter assembly according to claim 6 wherein the tubular dilator component comprises a lubricious plastic material.

* * * * *